United States Patent [19]

McCabe

[11] Patent Number: 5,146,932
[45] Date of Patent: Sep. 15, 1992

[54] ELASTIC COUNTERPRESSURE GARMENT

[76] Inventor: Francis J. McCabe, 239 Hastings Ct., Doylestown, Pa. 18901

[21] Appl. No.: 609,170

[22] Filed: Nov. 1, 1990

[51] Int. Cl.⁵ .......................... A61F 5/37; A61F 5/00
[52] U.S. Cl. ..................................... 128/873; 602/23; 128/DIG. 15
[58] Field of Search ............. 128/873, 87 R, 869–872, 128/78, DIG. 15, 89 R, DIG. 24, DIG. 20; 602/5, 19, 23, 6, 33, 36, 39; 2/2, 2.1 R, 2.1 A, DIG. 3, 46, 48, 69, 72, 114; 5/82 R

[56] References Cited

U.S. PATENT DOCUMENTS

| | | | |
|---|---|---|---|
| 3,744,053 | 7/1973 | Parker | 2/2.1 R |
| 3,823,712 | 7/1974 | Morel | 128/DIG. 20 |
| 3,933,150 | 1/1976 | Kaplan | 128/DIG. 20 |
| 3,993,056 | 11/1976 | Rabischong | 128/DIG. 20 |
| 4,276,341 | 6/1981 | Tanaka | 2/2.1 R |
| 4,325,148 | 4/1982 | Livernois | 2/2 |
| 4,455,683 | 6/1984 | Moretti | 2/2.1 A |
| 4,458,363 | 7/1984 | Harvey | 2/2.1 R |
| 4,700,407 | 10/1987 | Mattila | 2/2 |
| 4,946,453 | 8/1990 | Monson | 2/2.1 R |

*Primary Examiner*—Michael A. Brown
*Attorney, Agent, or Firm*—Frank J. Benasutti

[57] ABSTRACT

A bladder-less counterpressure garment primarily used in the treatment of a victim suffering from hypovolemic shock. The garment is made of a resilient material, like elastic, with a means for stretching the material to or near its stretch limit. This stretching supplies the requisite counterpressure to increase blood circulation to the vital organs.

6 Claims, 4 Drawing Sheets

ELASTIC COUNTERPRESSURE GARMENT

BACKGROUND OF THE INVENTION

1. Field of the Invention

This invention relates generally to body treatment care and specifically to counterpressure garments used in emergency treatment of victims suffering from hypovolemic shock and in the presence of intractable bleeding.

2. Description of the Prior Art

Shock is a life threatening condition that results when the body is unable to maintain circulation to the heart, lungs and brain. It may be caused by trauma, blood loss, toxins or other circulatory diminishment. In addition to the routine shock first-aid of lying the victim prone with the lower extremities raised to move blood to the critical organs, it is also known to apply surface counterpressure to the lower extremities sufficient to overcome the pressure in the capillary and venus system to force increased circulation to the critical organs.

Circumferential pneumatic counterpressure (CPC) devices are well known inflatable garments used to apply pressure around the arms, legs and/or abdomen to control intractable bleeding and ameliorate shock. Examples of such devices are described in U.S. Pat. No. 3,933,150 issued Jan. 20, 1976, to Kaplan et al., and U.S. Pat. No. 4,039,039 issued Aug. 2, 1977, to Gottfried. The application of a CPC device causes a dramatic rearrangement of the blood circulation within a victim's body. It causes the victim's blood pressure to rises and the volume of blood available to the heart, lungs and head to greatly increase, while the amount of blood in the extremities is decreased.

The safety of pneumatic CPC devices has been questioned because the garment can be over-pressurized and cause restriction of the respiratory process, acidosis or ischemic injury (where the garment presses the skin against underlying bone). A standard method of pressurizing a CPC is by using an air pump, which in the conditions and excitement surrounding an emergency situation, often result in the ambulance crew over-inflating the garment.

Another problem associated with CPC garments is the rapid pressure drop from the accidental puncturing of one or more bladders. A rapid depressurization could be fatal since the victim's blood pressure can decrease by as much as 60 mm Hg.

Pressurized garments are also susceptible to temperature and atmospheric pressure changes, forcing the ambulance crew to adjust the garment's pressure. For example, if a skier at the top of a mountain is involved in an accident and is placed in a CPC garment, the relative pressure within the garment's bladders will decrease when the skier is brought down to ground level; while outdoor to indoor temperature changes can also raise or lower the relative pressure.

Since the pneumatic pressure fittings are sometimes metallic, a victim might be X-rayed for possible fractures while in the garment. Further, the garment usually cannot be cut away in selected areas to expose portions of the victims body for treatment, as the cutting would open an air bladder and cause depressurization.

SUMMARY OF THE INVENTION

The present invention involves a counterpressure garment which utilizes elastic material in the legs and abdomen sections and adjustable fasteners to provide the external counterpressure necessary to transfer the blood supply back to the primary organs of a victim suffering from hypovolemic shock and possibly to slow or stop bleeding. The garment further utilizes a locatable abdomen flap containing a compressible foam block to provide appropriately direct counterpressure to the abdomen area.

An advantage of this garment over the pneumatic CPC garment is that the hazards of over-pressurization and sudden depressurization are eliminated. The garment is applied in a manner that applies circumferential pressure sequentially from the ankles to the lower torso to translocate blood toward the vital organs. It does not require metallic fittings, and therefore permits X-ray and other electromagnetic imaging while the victim remains under pressure. The perineal area remains open, and portions of the garment may be cut away in other areas to expose the victim's body for treatment or hypodermic insertion without loosing pressurization. Another advantage is that it is a durable and washable garment and sufficiently inexpensive to be disposable if exposed to dangerous bacteria.

A further advantage is that its pressure is not effected by temperature and atmospheric pressure changes. This independence from temperature and atmospheric pressure also makes this garment suitable for use as a "comfort" garment under Astronauts' space suits, to keep their blood pressure stable.

The foregoing and other objects, features and advantages of this invention will be apparent from the description of the preferred embodiment and the accompanying drawings.

DETAILED DESCRIPTION OF THE INVENTION

Figure 1:
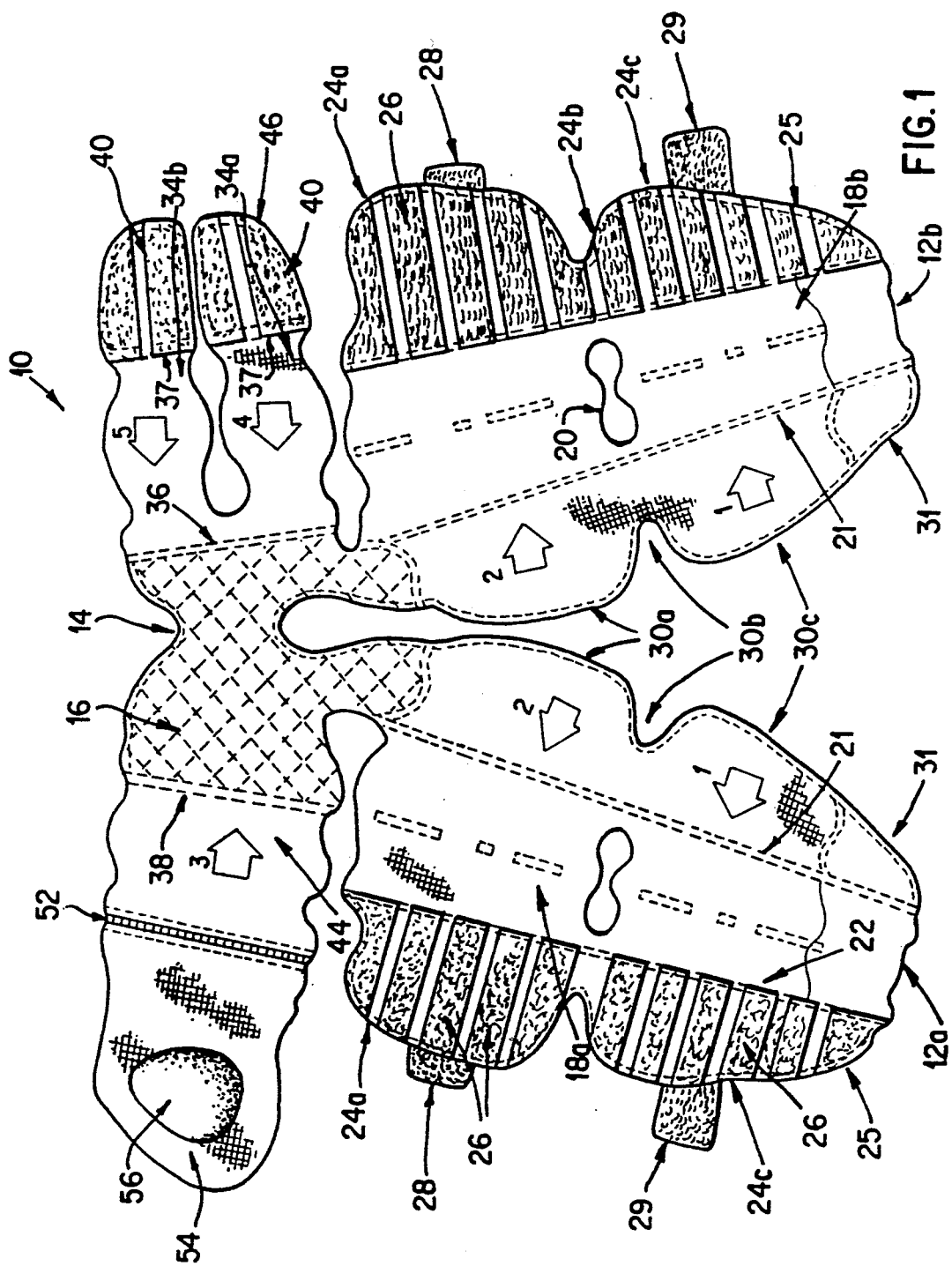
FIG. 1 is a perspective view of the inside of a counterpressure garment according to the invention, laid in a flat position.
Figure 2:
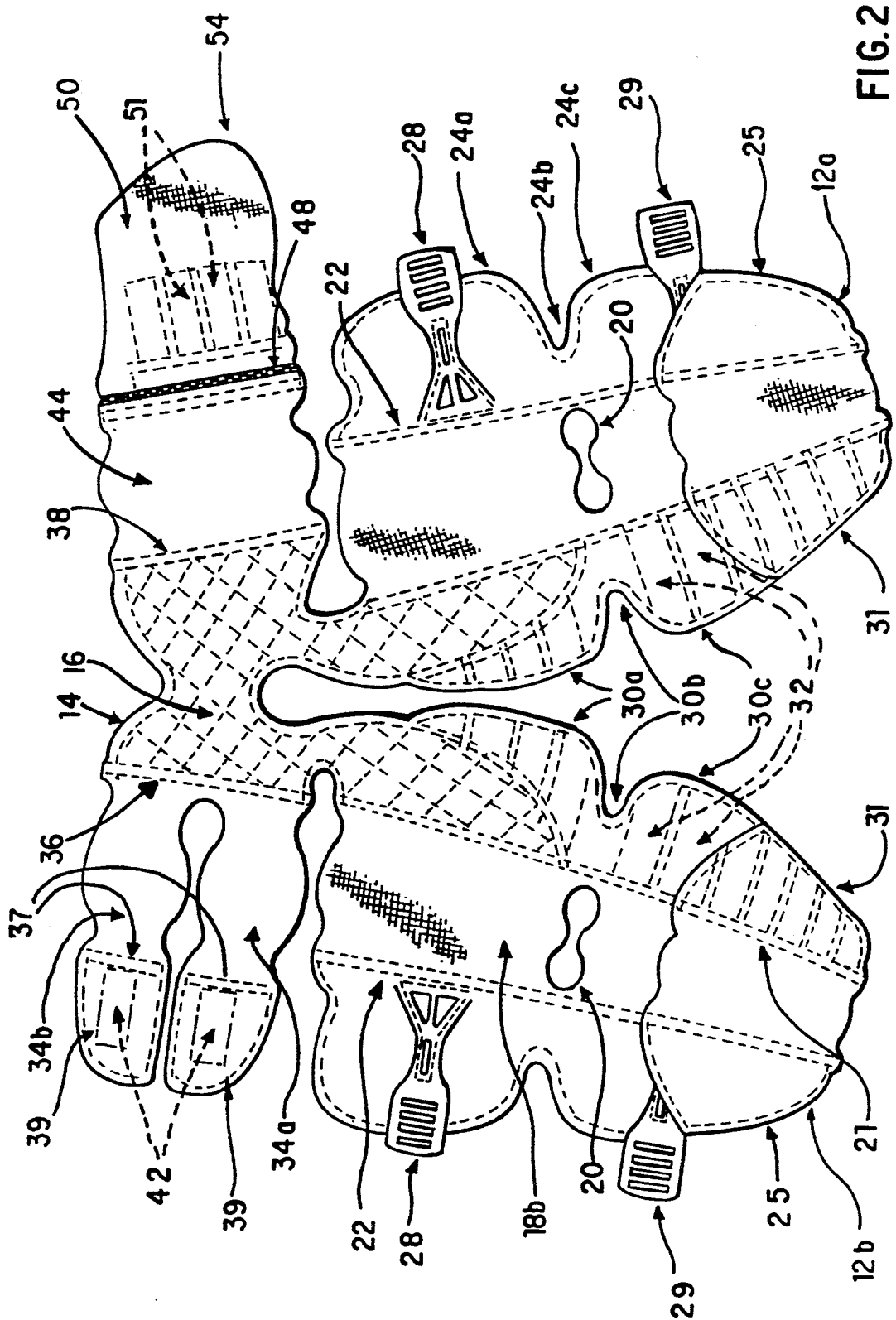
FIG. 2 is a perspective view of the outside of the counterpressure garment of FIG. 1, laid in a flat position.
Figure 3:
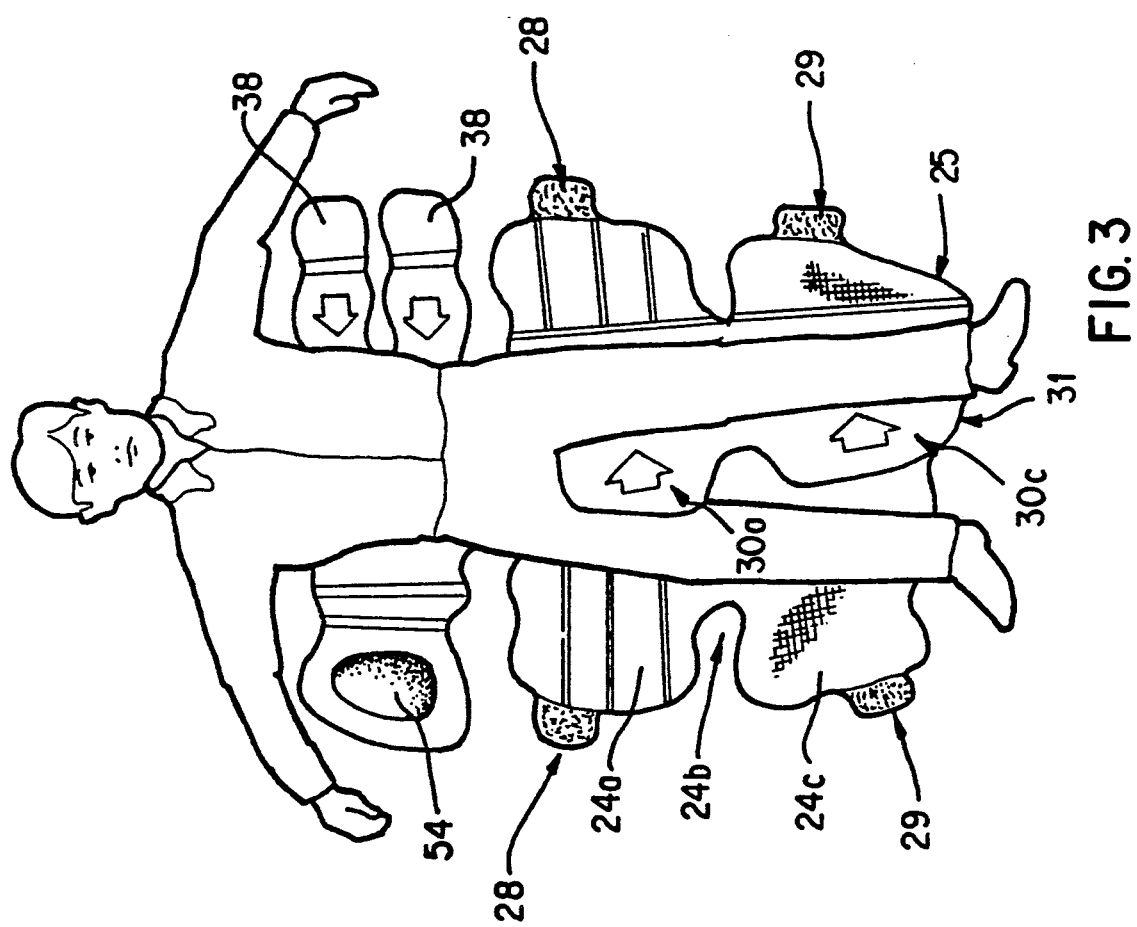
FIG. 3 is a perspective view of a victim laid on the counterpressure garment of FIG. 1.
Figure 4:
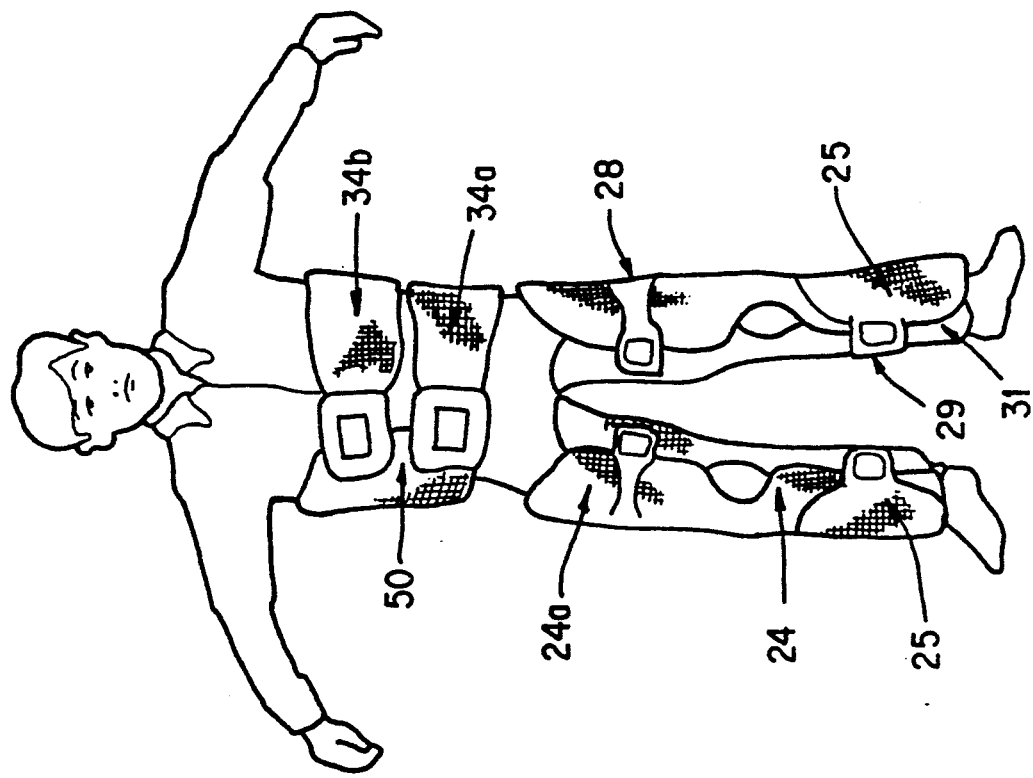
FIG. 4 is a perspective of a victim enclosed in the counterpressure garment of FIG. 1.

A counterpressure garment 10, depicted in a flat position in FIGS. 1 and 2, is adapted to be wrapped about a victim's legs and lower torso to apply external counterpressure to the lower circulatory system, as shown in FIGS. 3 and 4. A pair of leg sections 12a and 12b are adapted to enclose the victim's legs, while a lower torso section 14 is adapted to enclose the victim's lower torso and abdomen. Between the leg and lower torso sections, the perineal area remains exposed for hypodermic or tube insertion.

A center yoke 16 provides a foundation for both the leg and torso sections, and is preferably constructed of a foam core contained inside an impermeable cover for comfort and durability.

The leg sections 12a, 12b each include a center elastic band 18a, 18b which is preferably made of a core web of elastic material, such as coarse weave spandex, sandwiched loosely between an inner and outer cover, such as a neoprene cover. The neoprene material is used to allow screening of written directions onto the material and to protect the elastic material from damage and moisture. The neoprene covers are stitched to the edges of the elastic bands and are sufficiently loose to be expandable to a width equivalent to the elastic in a fully stretched condition. The elastic bands 18 have a dumbbell shaped cut-out 20 for the knee area to free the joint for movement. The elastic bands 18 are sewn at one edge to an inner support seam 21 of polypropylene webbing and at their other edge to a similar outer support seam 22. The yoke 16 is sewn to the upper section of the inner support seams 21, as shown in FIG. 2.

An outer flap 24 is sewn to the outer support seam 22. The flap 24 is contoured to a leg by having a wider upper section 24a for the thigh area, a narrow section 24b for the knee, and an intermediate width section 24c for the calf area. The thigh section 24a and the calf section 24c each have a plurality of evenly spaced horizontal velcro strips 26 sewn to their inside face, as depicted in FIG. 1. A pair of molded plastic pull tabs 28, 29 are attached directly to the outer support seam 22, one tab 28 over the center of the thigh section 24a, and the other tab 29 over the calf section 24c, for ease in stretching the elastic to or near its stretch limit in those areas.

An inner flap 30 is sewn to the inner support seam 21. The flap 30 is similarly contoured to the leg by a wider thigh section 30a, a narrow knee section 30b, and an intermediate width calf section 30c. The flap 30 has a plurality of spaced horizontal velcro strips 32 on its outer face, as shown in FIG. 2. The leg sections 12 are thus adapted to be tightly wrapped around the victim's legs by folding the inner flap 30 around the inside of the leg and then pulling the outer flap sections 24c, then 24a, one-at-a-time around the leg by the pull tabs 28, 29 sufficient to stretch the elastic band 18 to provide circumferential compression as the elastic seeks to return to its relaxed state limit, then mating the velcro strips 26 to the strips 32. Since the velcro strips on both the yoke and flap sections are horizontal, the mating can be made at different overlaps to accommodate various leg thickness while still stretching the elastic bands to provide circumferential compression. The stretched elastic provides the requisite counterpressure to the leg by attempting to contract to its relaxed length, thus compressing the leg on all circumferential sides.

The lower leg sections may also be provided with a second set of flaps 25, 31 outside of the flaps 24c and 30c, for the lower calf area, as shown in FIG. 2. The flaps 31 have horizontal velcro strips on their outside face, while the flaps 25 have the strips on their inside face, and are mated in the same manner as the flaps 24c and 30c to provide tighter mating over the lower calf and ankle area.

The lower torso section 14 has two elastic bands 34a, 34b sewn to a support seam 36 on one side of the yoke 16, and a single elastic band 44 sewn to a support seam 38 on the other side of the yoke. The elastic bands 34a, 34b and 44 each have a convex dumbbell shape and are also made of a elastic core sandwiched in neoprene, similar to the leg flaps. The two elastic bands 34a and 34b each have a support seam 37 supporting an end flap 39, which has a velcro pad 40 sewn on its inside face, as shown in FIG. 1, and a hand grip edge binding 46 made by stitching the material edges around a strip of batting cord. A polypropylene pull tab 42 is attached directly to the support seam 37 associated with each of the bands 34a and 34b.

The single band 44 terminates against an outer support seam 48, to which is also sewn a fastener flap 50 and a zipper flap 52. The fastener flap 50 has a plurality of spaced horizontal velcro strips 51 covering its outside face, as shown in FIG. 2. The zipper flap 52 supports one non-metallic zipper track. The matching non-metallic zipper track is attached to a removable abdomen compress 54, which comprises a compressible foam block 56 enclosed in a neoprene cover. The foam block 56 has a slight pear-shape to correspond roughly with the soft abdomen area between the rib cage. The abdomen compress is normally kept zipped to the garment, and is used whenever direct inward pressure on the abdomen is desired, such as to control suspected intra-abdominal hemorrhage. If direct abdomen pressure is not needed, the compress can be removed by the zipper. An excess of fabric can be used in the abdomen compress to permit sizing adjustments.

The zipper flap 52 is located inside from the fastener flap 50, such that the abdomen compress 54 can be placed over the victim's abdomen before the lower torso section 14 is fastened around the victim. The lower torso section 14 is wrapped around the victim by folding flap 50 inward, then pulling the bands 34a and 34b by their pull tabs 42 one-at-a-time around the torso to stretch the elastic, and then mating the velcro pads 40 to the horizontal velcro strips 51, at the overlap necessary to hold the elastic in a stretched condition. To achieve greater counterpressure about the abdomen, a removable stiffener plate or plates can be situated in the lower torso section.

Although not depicted in the drawings, it will be understood by those of ordinary skill that a gross size adjustment could be included to accommodate an exceptionally large or obese person by increasing the width of the elastic bands several inches in the leg and torso sections, and placing zipper tracks the same several inches apart on the elastic bands. The elastic material would then be folded to bring the zipper tracks together and zipped to produce an effective width for the normal adult body size, as depicted in the drawings. The zippers could then be opened before placing an extraordinarily large person in the garment to provide increased width.

In use, the counterpressure garment is laid flat as in FIG. 1, and the victim is placed face up on the garment with the top of the garment below the lowest rib, as shown in FIG. 3. Appropriate graphic markings and instructions, such as SPINE LINE, LEFT LEG and RIGHT LEG may be screened onto the neoprene surface to assist in placing the victim. The rescue personnel then kneel by the victim and enclose the legs by pulling the leg flaps to stretch the elastic and mating the velcro strips, as shown in FIG. 4. To translocate blood toward the vital organs, the calf flap 24c is mated first, then the lower calf flap 25, then the thigh flap 24a. If abdominal pressure is desired, the abdominal compress is placed over the soft abdomen area, and the lower torso flaps are pulled to stretch the elastic and fastened by the velcro strips.

If portions of the garment must be cut away to expose an area of the victim's body for treatment or insertion, the appropriate area can be marked, the flaps opened and the area cut out with a scissors, then refastened. Since there are no air bladders, cutting away material will not destroy counterpressure by the elastic in the covered areas. As the garment and zipper are all non-metallic, the patient can be X-rayed for fractures while in the garment.

I claim:

1. In a counterpressure garment for medical use by application to a patient, said garment having a pair of leg sections adapted to enclose the legs of a patient and a lower torso section adapted to enclose the lower torso and abdomen of a patient, the improvement comprising:

elastic material means in said leg and lower torso sections for providing when stretched, counterpressure to the circulatory system of said patient fastening means engaging the leg sections and lower torso sections for securing each section around a portion of the patient with the elastic material stretched; and each of said leg sections further comprising individual flap subsections that can be fasten together individually to provide a counterpressure to selected areas of the leg.

2. The counterpressure garment of claim 1, further comprising a flap containing a compressible block in hinged attachment to the lower torso section, said hinged attachment adapted to allow the block to be placed over a patient's abdomen before the lower torso section is positioned to enclose the patient.

3. The counterpressure garment of claim 1 wherein the fastening means comprises material made to grip on contact and mate with other material by the application of pressure to cause engagement of the two materials and mating and having sufficient dimensions to allow said material to be mated at varying overlapse sufficient to stretch the elastic material around parts of patients of different sizes.

4. The counterpressure garment of claim 3, further comprising a flap containing a compressible block in hinged attachment to the lower torso section, said hinged attachment adapted to allow the block to be placed over the patient's abdomen before the lower torso section is positioned to enclose the patient.

5. The invention of claim 3 wherein said leg sections comprise a plurality of subsections adapted to enclose the portion of the victim's leg sequentially from the ankle to the hip.

6. The invention of claim 1 wherein said leg sections comprise a plurality of subsections adapted to enclose the portion of the victim's leg sequentially from the ankle to the hip.

* * * * *